(12) United States Patent
Rudko et al.

(10) Patent No.: US 8,075,513 B2
(45) Date of Patent: Dec. 13, 2011

(54) PATIENT CONNECTION SYSTEM FOR A BALANCE HYDRATION UNIT

(75) Inventors: Robert I. Rudko, Holliston, MA (US); Mark R. Tauscher, Medfield, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 280 days.

(21) Appl. No.: 11/580,354

(22) Filed: Oct. 13, 2006

(65) Prior Publication Data
US 2008/0171966 A1 Jul. 17, 2008

(51) Int. Cl.
*A61M 1/00* (2006.01)
*A61M 31/00* (2006.01)

(52) U.S. Cl. .................. 604/29; 604/31; 604/65
(58) Field of Classification Search ........... 604/65–67, 604/29, 890.1, 31
See application file for complete search history.

(56) References Cited

U.S. PATENT DOCUMENTS

| | | |
|---|---|---|
| 3,954,010 A | 5/1976 | Hilblom |
| 4,132,644 A | 1/1979 | Kolberg |
| 4,146,029 A | 3/1979 | Ellinwood, Jr. |
| 4,204,957 A | 5/1980 | Weickhardt |
| 4,216,462 A | 8/1980 | McGrath et al. |
| 4,229,299 A | 10/1980 | Savitz et al. |
| 4,261,360 A | 4/1981 | Perez |
| 4,275,726 A | 6/1981 | Schael |
| 4,291,692 A | 9/1981 | Bowman et al. |
| 4,343,316 A | 8/1982 | Jespersen |
| 4,448,207 A | 5/1984 | Parrish |
| 4,449,538 A | 5/1984 | Corbitt et al. |
| 4,504,263 A | 3/1985 | Steuer et al. |
| 4,658,834 A | 4/1987 | Blankenship et al. |
| 4,712,567 A | 12/1987 | Gille et al. |
| 4,728,433 A | 3/1988 | Buck et al. |
| 4,813,925 A | 3/1989 | Anderson, Jr. et al. |
| 4,923,598 A | 5/1990 | Schal |
| 4,994,026 A | 2/1991 | Fecondini |

(Continued)

FOREIGN PATENT DOCUMENTS
EP   0258690   3/1988

(Continued)

OTHER PUBLICATIONS

Office Action of the Canadian Intellectual Property Office for Canadian Patent Application No. 2,579,829 mailed Jun. 13, 2008 (two (2) pages).

(Continued)

*Primary Examiner* — Theodore J Stigell
*Assistant Examiner* — Imani Hayman
(74) *Attorney, Agent, or Firm* — Iandiorio Teska & Coleman (57) ABSTRACT

A hydration management system includes a console for mounting on an IV pole. A urine collection bag and a hydration fluid bag hang from the console. Urine in the urine collection bag is weighed. An infusion pump is configured to pump hydration fluid from the infusion bag. A controller is responsive to the weight of the urine collection bag and controls the infusion pump to hydrate the patient based on the patient's urine output. An infusion set includes an infusion bag connector, an IV needle connector, and tubing, placed in the infusion pump, extending between the infusion bag connector and the IV needle connector. A urine collection set typically includes the urine collection bag, a catheter connector, and tubing extending between the urine collection bag connector and the catheter connector.

8 Claims, 5 Drawing Sheets

U.S. PATENT DOCUMENTS

| | | | |
|---|---|---|---|
| 5,098,379 | A | 3/1992 | Conway et al. |
| 5,176,148 | A | 1/1993 | Wiest et al. |
| 5,207,642 | A | 5/1993 | Orkin et al. |
| 5,722,947 | A * | 3/1998 | Jeppsson et al. .............. 604/29 |
| 5,769,087 | A | 6/1998 | Westphal et al. |
| 5,814,009 | A | 9/1998 | Wheatman |
| 5,891,051 | A | 4/1999 | Han et al. |
| 5,910,252 | A | 6/1999 | Truitt et al. |
| 5,916,153 | A | 6/1999 | Rhea, Jr. |
| 5,916,195 | A | 6/1999 | Eshel et al. |
| 5,981,051 | A | 11/1999 | Motegi et al. |
| 6,010,454 | A | 1/2000 | Arieff et al. |
| 6,171,253 | B1 | 1/2001 | Bullister et al. |
| 6,231,551 | B1 | 5/2001 | Barbut |
| 6,272,930 | B1 | 8/2001 | Crozafon et al. |
| 6,514,226 | B1 | 2/2003 | Levin et al. |
| 6,537,244 | B2 | 3/2003 | Paukovits et al. |
| 6,554,791 | B1 | 4/2003 | Cartledge et al. |
| 6,640,649 | B1 | 11/2003 | Paz et al. |
| 6,740,072 | B2 | 5/2004 | Starkweather et al. |
| 6,752,779 | B2 | 6/2004 | Paukovits et al. |
| 6,796,960 | B2 | 9/2004 | Cioanta et al. |
| 6,827,702 | B2 | 12/2004 | Lebel et al. |
| 6,942,637 | B2 | 9/2005 | Cartledge et al. |
| 7,029,456 | B2 | 4/2006 | Ware et al. |
| 7,044,002 | B2 | 5/2006 | Ericson et al. |
| 7,137,964 | B2 | 11/2006 | Flaherty |
| 7,278,983 | B2 | 10/2007 | Ireland et al. |
| 2002/0025597 | A1 | 2/2002 | Matsuda |
| 2002/0072647 | A1 | 6/2002 | Schock et al. |
| 2002/0107536 | A1 | 8/2002 | Hussein |
| 2002/0151834 | A1 | 10/2002 | Utterberg |
| 2002/0161314 | A1 | 10/2002 | Sarajarvi |
| 2003/0048185 | A1 | 3/2003 | Citrebaum et al. |
| 2003/0048432 | A1 | 3/2003 | Jeng et al. |
| 2003/0114786 | A1 | 6/2003 | Hiller et al. |
| 2004/0025597 | A1 | 2/2004 | Ericson et al. |
| 2004/0059295 | A1 | 3/2004 | Cartledge et al. |
| 2004/0081585 | A1 | 4/2004 | Reid |
| 2004/0087894 | A1 | 5/2004 | Flaherty |
| 2004/0122353 | A1 | 6/2004 | Shahmirian et al. |
| 2004/0133187 | A1 | 7/2004 | Hickle |
| 2004/0163655 | A1 | 8/2004 | Gelfand et al. |
| 2004/0167415 | A1 | 8/2004 | Gelfand et al. |
| 2004/0167464 | A1 | 8/2004 | Ireland et al. |
| 2004/0176703 | A1* | 9/2004 | Christensen et al. ......... 600/561 |
| 2004/0193328 | A1 | 9/2004 | Zaitsu et al. |
| 2004/0243075 | A1 | 12/2004 | Harvie |
| 2005/0027254 | A1 | 2/2005 | Vasko |
| 2005/0065464 | A1 | 3/2005 | Talbot et al. |
| 2005/0085760 | A1 | 4/2005 | Ware et al. |
| 2006/0052764 | A1 | 3/2006 | Gelfand et al. |
| 2006/0064053 | A1 | 3/2006 | Bollish et al. |
| 2006/0184084 | A1 | 8/2006 | Ware et al. |
| 2006/0235353 | A1 | 10/2006 | Gelfand et al. |
| 2006/0253064 | A1 | 11/2006 | Gelfand et al. |
| 2006/0270971 | A1 | 11/2006 | Gelfand et al. |
| 2007/0088333 | A1 | 4/2007 | Levin et al. |
| 2008/0027409 | A1 | 1/2008 | Rudko et al. |
| 2008/0033394 | A1 | 2/2008 | Gelfand et al. |
| 2008/0171966 | A1 | 7/2008 | Rudko et al. |
| 2008/0221512 | A1 | 9/2008 | Da Silva et al. |

FOREIGN PATENT DOCUMENTS

| | | |
|---|---|---|
| WO | WO 99/06087 | 2/1999 |
| WO | WO 2006/041496 A1 | 4/2006 |

OTHER PUBLICATIONS

Written Opinion of the International Searching Authority for PCT Application No. PCT/US05/08948 mailed Oct. 3, 2006 (five (5) pages).

Written Opinion of the International Searching Authority for PCT Application No. PCT/US2007/009683 mailed Nov. 24, 2008 (eight (8) pages).

Written Opinion of the International Searching Authority for PCT Application No. PCT/US07/09685 mailed Jul. 18, 2008 (twelve (12) pages).

Written Opinion of the International Searching Authority for PCT Application No. PCT/US07/09684 mailed Jul. 21, 2008 (nine (9) pages).

Written Opinion of the International Searching Authority for PCT Application No. PCT/US08/07845 mailed Sep. 17, 2008 (seven (7) pages).

Written Opinion of the International Searching Authority for PCT Application No. PCT/US08/07841 mailed Sep. 18, 2008 (six (6) pages).

Written Opinion of the International Searching Authority for PCT Application No. PCT/US09/02739 mailed Jun. 19, 2009 (six (6) pages).

Written Opinion of the International Searching Authority for PCT Application No. PCT/US2007/021791 mailed May 8, 2008 (nine (9) pages).

U.S. Appl. No. 12/798,940, Gelfand et al.

U.S. Appl. No. 12/800,674, Gelfand et al.

U.S. Appl. No. 12/800,673, Gelfand et al.

U.S. Appl. No. 12/800,699, Gelfand et al.

U.S. Appl. No. 12/800,698, Gelfand et al.

Written Opinion of the International Searching Authority; International Application No. PCT/US2010/000137 mailed Mar. 16, 2010, 8 pgs. (unnumbered).

Solomon et al., *Effects of Saline, Mannitol, and Furosemide on Acute Decreases in Renal Function Induced by Radiocontrast Agents*, The New England Journal of Medicine, vol. 331:1416-1420, Nov. 24, 1994 No. 21 (11 pages).

Weinstein, J.M., Heyman, S., Brezis, M., *"Potential Deleterious Effect of Furosemide in Radiocontrast Nephropathy"*, Nephron 1992; 62: 413-415.

Stevens et al., *"A Prospective Randomized Trial of Prevention Measures in Patients at High Risk for Contrast Nephropathy"* Journal of the American College of Cardiology, vol. 33, No. 2, Feb. 1999:403-411.

Urexact® 2000 System, mhtml:file:// C:\Documents%20and%20Settings\bob\Local%20Settings\ Temporary%20Int...(3 pages).

Bard Lubricath 3-Way Catheters, http://www.bardmedical.com/urology/cathtour/3way.html (1 page).

Foley Catheter Introduction, Foley Catheter, http://www.emedicinehealth.com/articles/11633-1.asp; http://www.emedicinehealth.com/articles/11633-8.asp (2 pages).

Gambro Acute Renal Failure, Prisma Machine, http://www.gambro.com/Page.asp?id=2446; http://www.gambro.com/upload/press_media_toolkit/download_images/Prisma.jpg (2 pages).

Angiometrix, The Metricath System, http://www.angiometrx.com/Metricath%20System.htm (1 page).

Merit Medical Systems, Inc. 2003 Annual Report; Balloon Inflation Devices & Pressure Monitoring Syringes; Transducers and Accessories, http://www.corporatewindow.com/annuals/mmsi03/10kpage5.html (3 pages).

Cardiovascular Mikro-Tip Pressure Transducer Catheters, http://www.millarinstruments.com/products/cardio/cardio_sngldual.html (5 pages).

Infusion Dynamics The Power Infuser, http://www.infusiondynamics.com/powerinfuser/ (2 pages).

Ultra-Low Profile Single Point Load Cell—S215, http://smdsensors.com/detail_pgs/s215.htm (2 pages).

Rihal et al., *Incidence and Prognostic Importance of Acute Renal Failure After Percutaneous Coronary Intervention*, Circulation, May 14, 2002, pp. 2259-2264.

Wakelkamp et al., *The influence of drug input rate on the development of tolerance to frusemide*, Br. J. Clin. Pharmacol 1998; 46:479-487, pp. 479-487.

Rosamilia et al., *"Electromotive Drug Administration of Lidocaine and Dexamethasone Followed by Cystodistension in Women With Interstitial Cystitis"*, International Urogynecological Journal Pelvic Floor Dysfunction 1997; 8(3): Abstract of pp. 142-145.

Lelarge et al., *"Acute Unilateral Renal Failure and Contralateral Ureteral Obstruction"*, American Journal of Kidney Diseases, vol. XX, No. 3, Sep. 1992, pp. 286-288.

Doty et al., "*Effect of Increased Renal Venous Pressure on Renal Function*", Journal of Trauma: Injury, Infection and Critical Care, vol. 47, No. 6, Dec. 1999, pp. 1000-1003.

Edelson et al., "*Pharmacokinetics of Iohexol, a New Nonionic Radiocontrast Agent, in Humans*", Journal of Pharmaceutical Sciences, vol. 73, No. 7, Jul. 1984, pp. 993-995.

Hvistendahl et al., "*Renal Hemodynamic Response to Gradated Ureter Obstruction in the Pig*", Nephron 1996; 74, pp. 168-174.

Pedersen et al., "*Renal Water and Sodium Handling During Gradated Unilateral Ureter Obstruction*", Scand J Urol Nephrol 2002; 36, pp. 163-172.

Brezis et al., "*Hypoxia of the Renal Medulla—its Implications for Disease*" New England Journal of Medicine, vol. 322, No. 10, Mar. 9, 1995 pp. 647-655.

Heyman et al., "*Pathophysiology of Radiocontrast Nephropathy: A Role for Medullary Hypoxia*", Investigative Radiology, vol. 34, No. 11, Nov. 1999, pp. 685-691.

James M. Gloor and Vincente E., *Reflux and Obstructive Nephropathy*, Atlas of Diseases of the Kidney, on-line edition, vol. Two, Section I, Ch. 8, pp. 8.1-8.25 (date unknown).

\* cited by examiner

PATIENT CONNECTION SYSTEM FOR A BALANCE HYDRATION UNIT

FIELD OF THE INVENTION

This subject invention relates to a balanced hydration system.

BACKGROUND OF THE INVENTION

The applicant has devised a balanced hydration system wherein a control unit monitors the patient's urine output and provides hydration fluid to the patient based on the patient's urine output. See published U.S. Patent Application Serial No. US2006/0052764A1 incorporated herein by this reference.

One embodiment of such a system requires both an infusion tubing set extending between a hydration fluid bag and an IV needle inserted into the patient and also a urine collection tubing set extending between a urine collection bag and a catheter inserted in the patient.

Currently, no commercially available tubing set includes both an infusion tubing set and a urine collection tubing set; nor are the separate infusion tubing and urine collection sets commercially available suitable for use with the applicant's system.

Moreover, it is preferred for priming of the tubing and for system initialization that the urine collection tubing set be connected to the infusion tubing set. No commercially available product provides such an interconnection.

In addition, during replacement of an empty infusion fluid bag, it is possible that a full infusion fluid bag might be hung by a nurse or attendant at an elevation higher than the patient creating a "free flow" condition where infusion fluid is injected into a patient unintentionally.

Finally, it may not be obvious to a nurse or attendant how the infusion tubing and/or the urine collection tubing sets are to be used, interfaced with the balanced hydration control unit, and/or connected between the patient and the urine collection and infusion fluid bags.

SUMMARY OF THE INVENTION

It is therefore an object of this invention to provide a sterile infusion tubing set and urine collection tubing set for use with a balanced hydration system.

It is a further object of this invention to provide such a patient connection system which facilitates priming and initialization of the balanced hydration system.

It is a further object of this invention to provide such a patient connection system which prevents free flow conditions.

It is a further object of this invention to provide such a patient connection system which is easy to use.

The subject invention results from the realization that a novel patient connection system for a balanced hydration unit includes, in the preferred embodiment, both a urine collection set and an infusion tubing set in a sterile sealed bag along with a priming set, a check valve which prevents free flow of the infusion fluid, and coding which assists the nurse or attendant in properly connecting the infusion set and the urine collection set.

The subject invention, however, in other embodiments, need not achieve all these objectives and the claims hereof should not be limited to structures or methods capable of achieving these objectives.

This invention features a hydration management system comprising a console for mounting on an IV pole, a first attachment extending from the console for hanging a urine collection bag, a first weighing device in the console responsive to the first attachment for weighing the urine collection bag, a second attachment extending from the console for hanging a source of hydration fluid in an infusion bag, and a second weighing device in the console responsive to the second attachment for weighing the infusion bag.

An infusion pump is integrated with the console and configured to pump hydration fluid from the infusion bag into a patient. A controller is responsive to the first and second weighing devices and is configured to control the infusion pump to hydrate the patient based on the patient's urine output.

An infusion set includes an infusion bag connector, an IV needle connector, and tubing extending between the infusion bag connector and the IV needle connector. A urine collection set includes a urine collection bag connector, a catheter connector, and tubing extending between the urine collection bag connector and the catheter connector.

Preferably, the system further includes a priming set having a connector configured to receive the IV needle connector of the infusion set and an adapter connected to the IV needle connector and configured to receive the catheter connector of the urine collection set. The infusion set may further include a check valve between the IV needle connector and the infusion bag connector to prevent gravity flow of infusion fluid into the patient. Also, the infusion set and the urine collection sets may be coded and there may be a map depicting the proper installation of the coded infusion and urine collection sets.

The infusion set may further include a pressure transducer leg for interconnecting the infusion set tubing to a pressure transducer on the console.

The subject invention also features a patient connection system for a balanced hydration unit. An infusion set includes an infusion bag connector, a luer connector for receiving an IV needle, and tubing extending between the infusion bag connector and the luer connector. A urine collection set includes a urine collection bag, a catheter connector, and tubing extending between the urine collection bag and the catheter connector. A sealable bag stores both the infusion set and the urine collection set therein in a sterile fashion until ready for use.

The system may further include a priming set having a luer connector configured to receive the luer connector of the infusion set, and an adapter connected to the luer connector and configured to receive the catheter connector of the urine collection set.

The infusion set may further include a check valve between the luer connector and the infusion bag connector to prevent gravity flow of infusion fluid into the patient. Typically, the check valve is a one way check valve and configured to prevent flow in the tubing towards the IV needle connector. The hydration unit preferably includes an infusion pump operable to pump fluid from an infusion bag through the infusion set tubing to the luer connector at a pressure $P_0$. The check valve is configured to open at a predetermined pressure $P_1$ than or equal to $P_0$. In one example, $P_0$ is approximately 5 psi and $P_1$ is between approximately 1.5 to 3.5 psi.

The infusion set and the urine collection set are preferably coded and a map may be provided depicting the proper installation of the coded infusion and urine collection sets. In one example, the infusion set and the urine collection set are color coded and/or coded via numbers and/or letters.

The infusion set may further include a pressure transducer leg for interconnecting the infusion set tubing to a pressure transducer. In one example, the pressure transducer leg includes a T-connector in the infusion set tubing, a pressure transducer connector, and tubing extending between the T-connector and the pressure transducer connector. The pressure transducer leg may also include a filter. Or, the pressure transducer may be a part of the infusion set.

The infusion set may further include one or more pinch clamps for the infusion tubing and/or one or more injection ports for the infusion tubing. In addition, absorbent material may be included in the urine collection bag. And, the urine collection set may include one or more pinch clamps for the urine collection tubing and/or one or more injection ports for the urine collection tubing.

The urine collection bag typically includes a drain port. In one preferred embodiment, the urine collection bag drain port includes a drainage valve biased in the closed position. This valve would require that the user hold the valve open while draining the urine bag. When the user releases the drain valve, the drain port closes, preventing urine from being lost if the user were to walk away and forget to close the valve.

In one embodiment, the patient connection system for a balanced hydration unit comprises an infusion set including: an infusion bag connector, an IV needle connector, and tubing extending between the infusion bag connector and the IV needle connector; a urine collection set including: a urine collection bag connector, a catheter connector, and tubing extending between the urine collection bag and the catheter connector; and a priming set configured to connect the IV needle connector of the infusion set to the catheter connector of the urine collection set.

In one embodiment, a patient connection system for a balanced hydration unit comprises an infusion set including: an infusion bag connector, an IV needle connector, tubing extending between the infusion bag connector and the IV needle connector, and a check valve between the IV needle connector and the infusion bag connector for preventing gravity flow of infusion fluid into a patient; and a urine collection set including: a urine collection bag connector, a catheter connector, and tubing extending between the urine collection bag and the catheter connector.

In one embodiment, a patient connection system for a balanced hydration unit comprises an infusion set including: an infusion bag connector, an IV needle connector, and tubing extending between the infusion bag connector and the IV needle connector; a urine collection set including: a urine collection bag connector, a catheter connector, and tubing extending between the urine collection bag and the catheter connector; the infusion set and the urine collection set being coded; and a map depicting the proper installation of the coded infusion and urine collection sets.

The typical infusion set includes an infusion bag spike, a luer connector for receiving an IV needle, and tubing extending between the infusion bag spike and the luer connector. The typical urine collection set includes a urine collection bag connector, a Foley catheter connector, and tubing extending between the urine collection bag and the Foley catheter connector.

The subject invention also features a patient connection kit for a balanced hydration unit. The kit comprises an infusion set including an infusion bag connector, an IV needle connector adapted to connect to an IV needle, and tubing extending between the infusion bag connector and the connector. The infusion set is adapted to be connected between the IV needle and an infusion bag and interconnected with the balanced hydration unit. The kit also includes a urine collection set including a urine collection bag connector, a catheter connector adapted to connect to a catheter, and tubing extending between the urine collection connector and the catheter connector. The urine collection set is adapted to be connected between a urine collection bag and the catheter.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

A patient hydration system according to this invention is typically mounted on IV pole 84 and includes balancing unit 34 with programmable controller electronics and weighing mechanisms therein. Source of infusion fluid bag 24 is hung on hook 92 and urine collection bag 52 is hung on hook 90. Unit 34 includes one or more weight scales such as an electronic strain gage or other means to periodically detect the weight of the collected urine 26 in bag 52 and, if desired, the weight of the remaining hydration fluid 27 in bag 24. Hooks 90 and 92 are connected to a system of levers which translates force to a scale such as a strain gage within unit 34. The strain gage converts force into an electronic signal that can be read by a controller. Suitable electronic devices for accurately measuring the weight of a suspended bag with urine are available from Strain Measurement Devices, 130 Research Parkway, Meriden, Conn., 06450. These devices include electronic and mechanical components necessary to accurately measure and monitor weight of containers with medical fluids such as one or two-liter plastic bags of collected urine. For example, the overload proof single point load cell model S300 and the model S215 load cell from Strain Measurement Devices are particularly suited for scales, weighing bottles or bags in medical instrumentation applications. Options and various specifications and mounting configurations of these devices are available. These low profile single point sensors are intended for limited space applications requiring accurate measurement of full-scale forces of 2, 4, and 12 pounds-force. They can be used with a rigidly mounted platform or to measure tensile or compressive forces. A 10,000 Ω wheatstone bridge offers low power consumption for extended battery life in portable products. Other examples of gravimetric scales used to balance medical fluids using a controller controlling the rates of fluid flow from the pumps in response to the weight information can be found in U.S. Pat. Nos. 5,910,252; 4,132,644; 4,204,957; 4,923,598; and 4,728,433 incorporated herein by this reference.

It is understood that there are many ways known in the art of engineering to measure weight and convert it into computer inputs. Regardless of the implementation, the purpose of the weight measurement is to detect the increasing weight of the collected urine 26 in the bag 52 and to adjust the rate of infusion or hydration based on the rate of urine flow.

Unit console 34 is also typically equipped with the user interface. The interface allows the user to set (dial in) the two main parameters of therapy: the duration of hydration and the desired net fluid balance at the end. The net fluid balance can be zero if no fluid gain or loss is desired. Display indicators on the console show the current status of therapy: the elapsed time 100 and the net fluid gain or loss 102.

The user interface may also include alarms 104. The alarms notify the user of therapy events such as an empty fluid bag or a full collection bag as detected by the weight scale. In one proposed embodiment, the urine is collected by gravity. If urine collection unexpectedly stops for any reason, the system will reduce and, if necessary, stop the IV infusion of fluid and alarm the user. Alternatively, the console can include the second (urine) pump similar to infusion pump 22. This configuration has an advantage of not depending on the bag height for drainage and the capability to automatically flush the catheter if it is occluded by temporarily reversing the pump flow direction.

Infusion pump 22 pumps infusion fluid from bag 24 into the patient and is controlled by the controller electronics within the unit which monitors the weight of urine 26 in urine collection bag 52. In this way, the patient is properly hydrated and the infusion rate of infusion pump 22 is automatically adjusted to achieve, as necessary, a zero, positive, or negative net fluid balance in the patient.

The electronic controller may also incorporate a more advanced feature allowing the physician to set a desired (for example positive) hydration net goal. For example, the physician may set the controller to achieve positive net gain of 400 ml in 4 hours. The controller calculates the trajectory and adjusts the infusion pump flow rate setting to exceed the urine output accordingly. For example, to achieve a positive net gain of 400 ml over 4 hour, the controller may infuse 25 ml of hydration fluid every 15 minutes in addition to the volume of urine made by the patient in each 15 minute interval. See also co-pending U.S. application Ser. Nos. 11/408,391; 11/408,851; and 11/409,171 filed Apr. 21, 2006 which are incorporated herein by this reference.

Figures 1, 2:
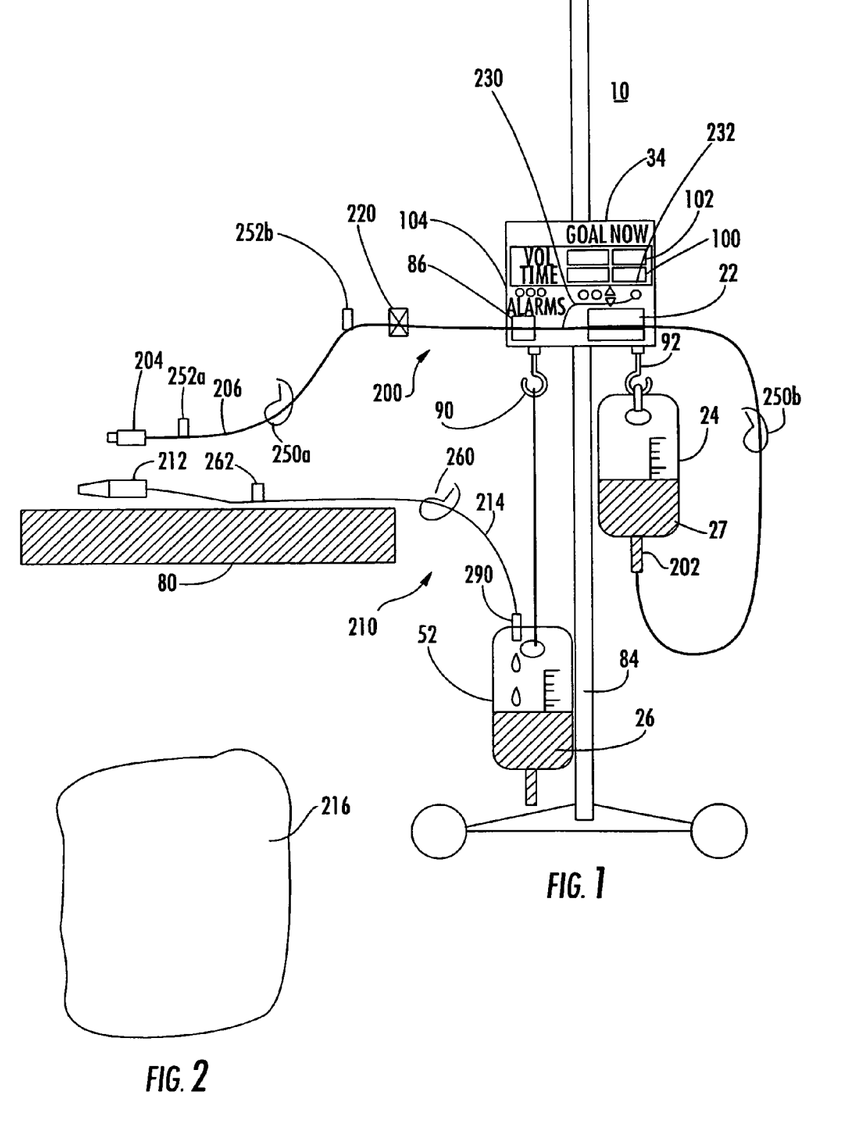
FIG. 1 is a highly schematic front view showing one example of a balanced hydration system and infusion fluid and urine collection tubing sets in accordance with the subject invention.
FIG. 2 is a schematic depiction of a sealable bag for the disposable infusion fluid and urine collection sets shown in FIG. 1.

In accordance with this invention, infusion set 200 includes infusion bag "spike" connector 202 received in infusion fluid bag 24, luer connector 204 for receiving an IV needle, and tubing 206 extending therebetween. Urine collection set 210 typically includes urine collection bag 52, Foley catheter connector 212 for connection to a Foley catheter, and tubing 214 extending between urine collection bag connector 290 and connector 212. Infusion set 200 and urine collection set 210 are placed together as a kit for the hydration unit in sealed bag 216, FIG. 2 for storage in a sterile fashion until ready for use.

Figure 3:
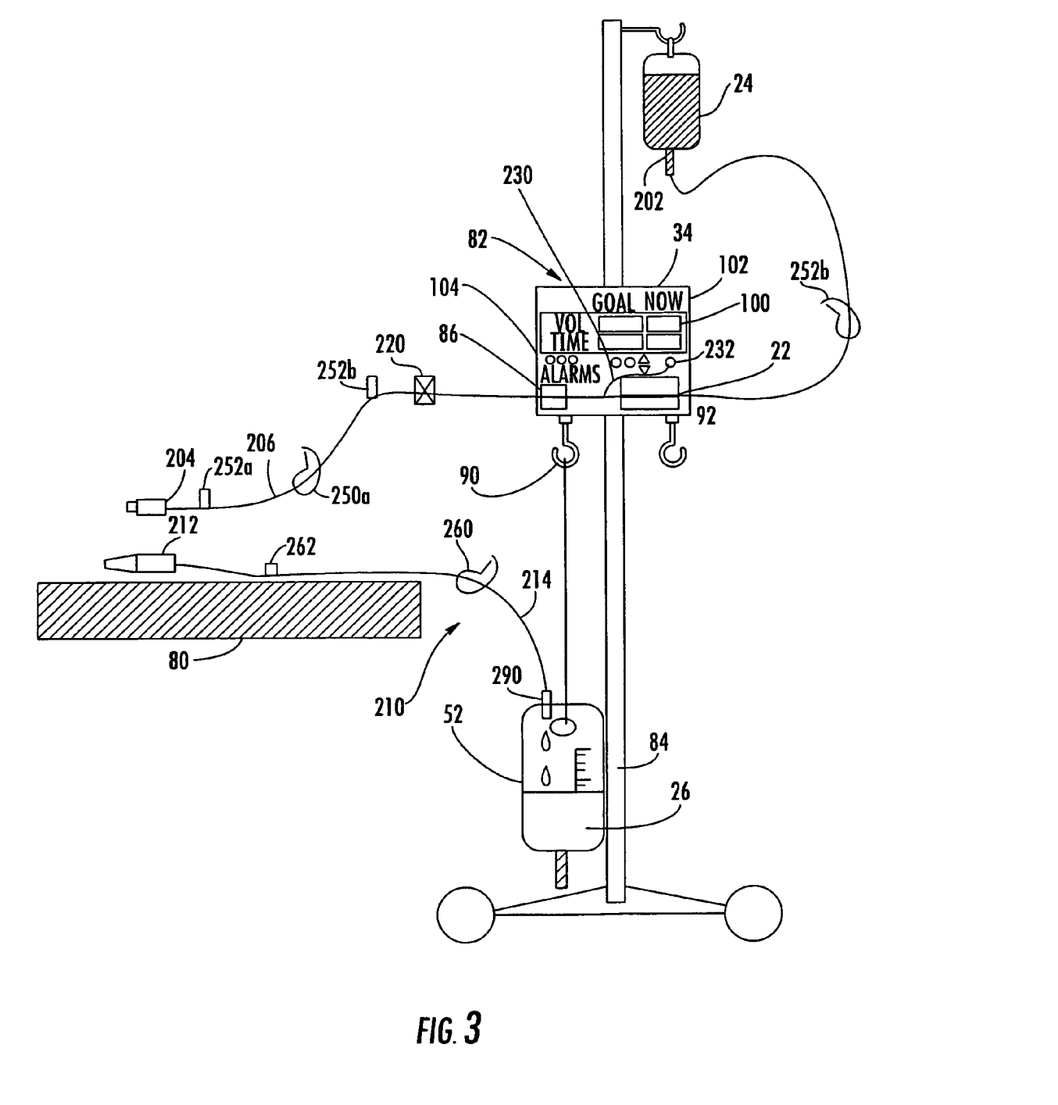
FIG. 3 is a schematic depiction of a balanced hydration system similar to that shown in FIG. 1 except now the infusion bag has been hung at an elevation higher than the patient.

Infusion set 200 preferably includes one way check valve 220 configured to prevent flow in the tubing towards infusion fluid bag 24 and also to prevent gravity flow of infusion fluid into the patient when, for example, a nurse or attendant hangs infusion fluid bag 24 above the elevation of the patient as shown in FIG. 3. Preferably, check valve 220 is configured to prevent flow unless a pressure $P_1$ is present in tubing 206 downstream of infusion pump 22. Infusion pump 22 pumps infusion fluid at a pressure of $P_0$. The condition shown in FIG. 3, without pump 22 operating, establishes a pressure in tubing 206 of $P_g$. Preferably, $P_g < P_1 \leq P_0$. In one example, $P_g$ was 1.3 psi and $P_0$ was 5 psi. Check valve 220, in one example, was a 1.5 .to 3.5 psi check valve available from Smart Products Corporation.

In one example, infusion set 200 also includes a pressure transducer leg 230 for connecting tubing 206 to pressure transducer 232 of balancing unit 34. Infusion set 200 may also include pinch clamps 250a and 250b and one or more injection port fittings 252a and 252b. Similarly, urine collection set 210 may include pinch clamp 260 and sampling port fitting 262. In another example, the transducer leg may include an in-line, disposable pressure sensor such as the sensors available from Merit Medical (Salt Lake City, Utah). Line 230 would then be an electrical connection between the sensor and unit console 34.

Figure 4:
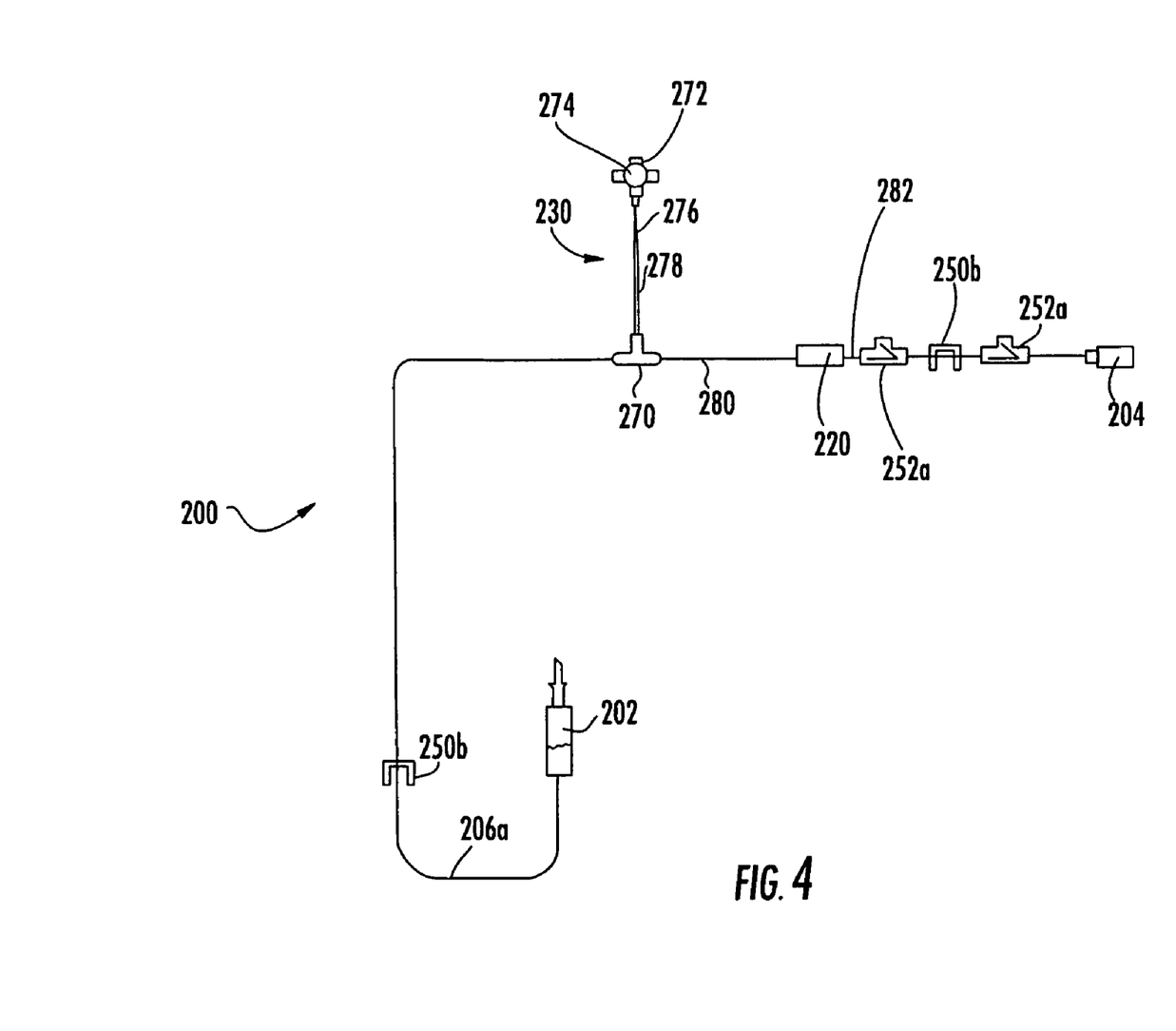
FIG. 4 is a more detailed schematic view of one preferred example of an infusion set in accordance with the subject invention.
Figure 5:
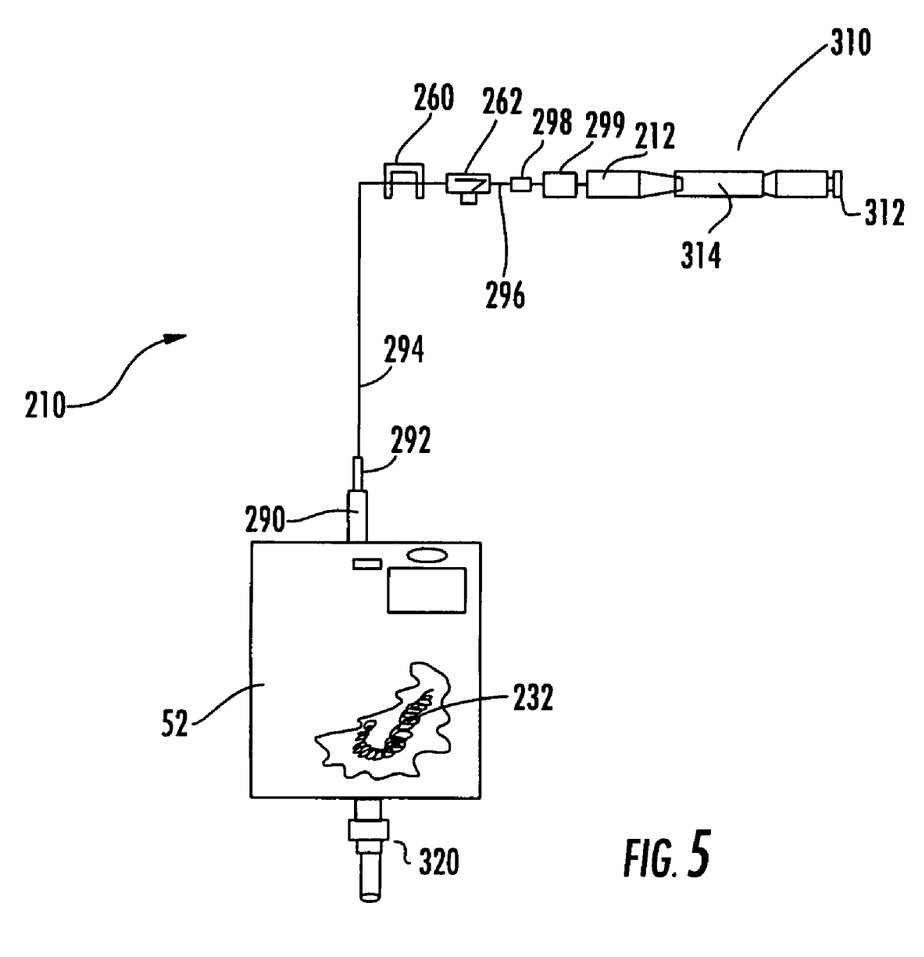
FIG. 5 is a more detailed schematic view of one preferred example of a urine collection set in accordance with the subject invention.

FIGS. 4-5 show, in more detail, these and other features of infusion set 200 (FIG. 4) and urine collection set 210 (FIG. 5). Infusion set 200, FIG. 4 typically includes infusion bag spike 202, 47" of PVC tubing 206a ⅛" ID, ¼" OD extending therefrom, clamp 250b on tubing 206a, and T-connector 270 of pressure transducer leg 230 downstream of the location where tubing 206a is inserted into pump 22, FIG. 1. Pressure transducer leg 230 is 4.5" in length and extends to pressure transducer connector 272. Transducer leg 230 includes hydrophobic filter 274, ⅛" ID, ¼" OD PVC tubing 276 and ¼" ID, ⅜" OD tubing 278. 4.75" of ⅛" ID, ¼" OD PVC tubing 280 extends between T-connector 270 and check valve 220 and is designed to be placed in air detector 86 of hydration unit 34, FIG. 1. The remainder of PVC tubing 282 is 83" long, ⅛" ID, 3/16" OD, and terminates in luer connector 204 which receives the male luer portion of a standard IV needle set.

Urine collection set 210, FIG. 5 includes a short length of ⅜" ID, 7/16" OD PVC tubing 290 extending from urine collection bag 52, a short length of ¼" ID, ⅜" OD PVC tubing 292 connected therewith, and 72" of ⅛" ID, ¼" OD PVC tubing 294 extending therefrom. Downstream of injection port fitting 262 is a short length of ⅛" ID, ¼" OD tubing 296 followed by a short length of ¼" ID, ⅜" OD tubing 298 followed by ⅜" ID, 7/16" OD tubing 299 connected to Foley catheter adapter 212. An injection port fitting can also be included as port of Foley catheter adapter 212. An extension section can be provided to lengthen tubing section 294 in cases where a longer distance is desirable between bag 52 and adapter 212.

FIG. 5 also shows priming set 310 including luer connector 312 configured to receive luer connector 204 of infusion set 200, FIG. 4. Adapter 314, FIG. 5 (e.g., a short length of PVC tubing ⅜" ID and 7/16" OD) connects luer connector 312 to Foley connector 212. In this way, the infusion set output can be connected to the urine collection set input during system priming, set-up, and an initialization.

In one embodiment, urine collection bag 52 includes a typical drain tube with a clamp thereon. But, in the preferred example, bag 52 includes drain port 320 with a valve biased in the closed position to prevent inadvertent drainage. Such a valve is available from the Qosina Corporation.

Also, absorbent material 322 such as sodium polyacrylate may be disposed in urine collection bag 52 to prevent messes and to render drainage of the collection bag unnecessary.

Figure 6:
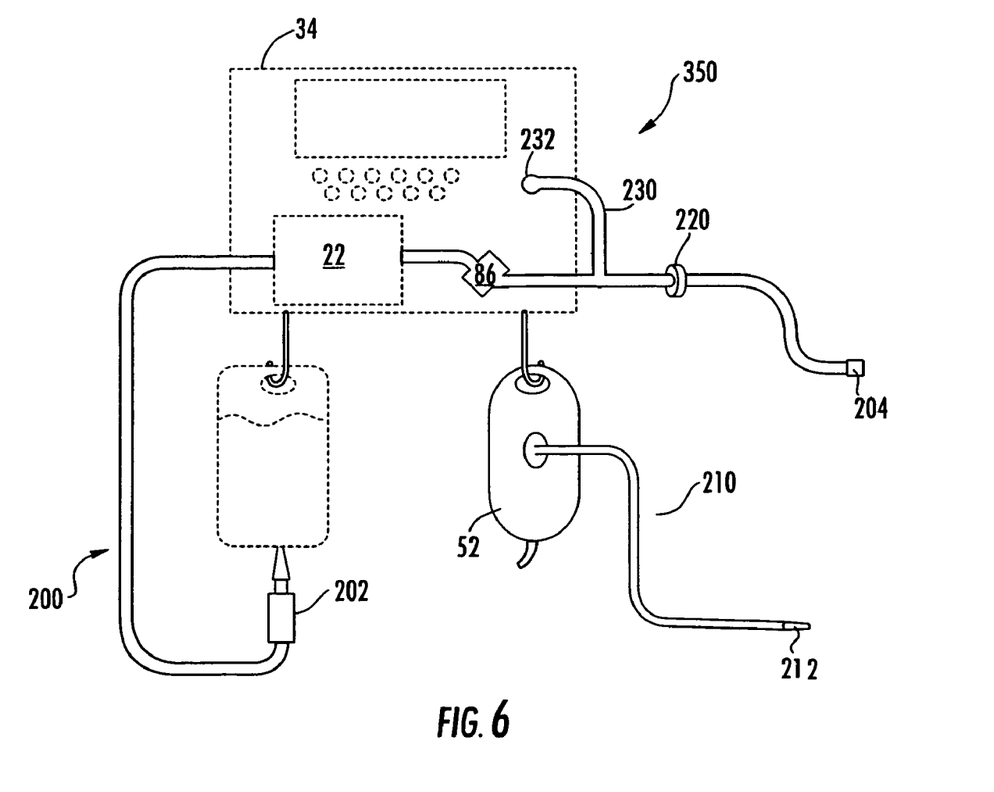
FIG. 6 is a schematic front view showing how urine collection set and infusion set can be differently coded to assist the nurse or attendant in properly connecting the same.

FIG. 6 depicts, in phantom, a prototype balanced hydration unit 34. To assist in installation, the tubing of urine collection set 210, FIG. 6 is coded differently, for example color coded differently, than the tubing of infusion set 200 and map 350 is provided, on either the hydration unit itself or as a separate placard, depicting the proper routing of the two tubing sets as shown in FIG. 6. Also, infusion pump 22 could be colored blue, for example, and the section of tubing of infusion set 200 designed to be placed in infusion pump 22 also colored blue. Air detector 86 could be colored a different color, green for example, and the section of infusion set tubing designed to pass through air detector 86 also colored green. Similarly, pressure transducer 232 could be colored still a different color, red for example, and transducer leg 230 of infusion set 200 also colored red. Also, priming set 310, FIG. 5 could be color coded in a special way. The tubing sets, however, could be coded using other than color using for example, numbering and/or lettering.

Combined infusion tubing and urine collection tubing sets for use with the balanced hydration system are thus provided in a sterile manner and preferably include a priming set which facilitates priming of the balanced hydration system. The patient connection system of the subject invention prevents free flow conditions and is easy to use. The patient connection system for a balanced hydration unit includes, in the preferred embodiment, both a urine collection set and an infusion tubing set in a sterile sealed bag along with a priming set, a check valve which prevents free flow of the infusion fluid, and coding which assists the nurse or attendant in properly connecting the infusion set and the urine collection set.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A hydration management system comprising:
   a console for mounting on an IV pole;
   a first attachment extending from the console for hanging a urine collection bag;
   a first weighing device in the console responsive to the first attachment for weighing the urine collection bag;
   a second attachment extending from the console for hanging a source of hydration fluid in an infusion bag;
   a second weighing device in the console responsive to the second attachment for weighing the infusion bag;
   an infusion pump integrated with the console and configured to pump hydration fluid from the infusion bag;
   a controller in the console, responsive to the first and second weighing devices, and configured to control the infusion pump to hydrate the patient based on the patient's urine output;
   an infusion set connected to the infusion bag and including an IV needle connector; and
   a urine collection set connected to the urine collection bag and including a catheter connector; and
   a system priming set having:
      a connector configured to receive the IV needle connector of the infusion set, and
      an adapter for connection to the connector and configured to receive the catheter connector of the urine collection set to drive hydration fluid in the infusion bag into the urine collection bag.

2. The system of claim 1 in which the infusion set further includes a check valve between the IV needle connector and an infusion bag connector to prevent gravity flow of infusion fluid into the patient.

3. The system of claim 1 in which the infusion set and the urine collection sets are coded.

4. The system of claim 3 further including a map depicting the proper installation of the coded infusion and urine collection sets.

5. The system of claim 1 in which the infusion set further includes a pressure transducer leg for interconnecting infusion set tubing to a pressure transducer on the console.

6. A patient connection system for a balanced hydration unit, the system comprising:
   an infusion set extending from an infusion bag to a patient IV needle and including:
      an infusion bag connector,
      an IV needle connector, and
      tubing extending between the infusion bag connector and the IV needle connector;
   a urine collection set extending from a patient catheter to a urine collection bag and including:
      a urine collection bag connector,
      a catheter connector, and
      tubing extending between the urine collection bag and the catheter connector; and
   a priming set configured to connect the IV needle connector of the infusion set to the catheter connector of the urine collection set to drive infusion fluid from the infusion bag into the urine collection bag before connection of the infusion set and the urine collection set to the patient.

7. The system of claim 6 in which the IV needle connector is a luer connector and the catheter connector is a Foley catheter connector.

8. The system of claim 6 in which the priming set includes:
   a luer connector configured to receive the luer connector of the infusion set, and
   an adapter connected to the luer connector and configured to receive the catheter connector of the urine collection set.

* * * * *